US00PP07991P

United States Patent [19]

Stravers

[11] Patent Number: Plant 7,991

[45] Date of Patent: Sep. 29, 1992

[54] GERBERA PLANT NAMED TERTALA

[75] Inventor: Lambertus J. M. Stravers, Kudelstaart, Netherlands

[73] Assignee: Terra Nigra BV, De Kwakel, Netherlands

[21] Appl. No.: 645,603

[22] Filed: Jan. 25, 1991

[51] Int. Cl.[5] ..... A01H 5/00

[52] U.S. Cl. ..... Plt./68.1

[58] Field of Search ..... Plt./68

*Primary Examiner*—James R. Feyrer

*Attorney, Agent, or Firm*—Foley & Lardner

[57] ABSTRACT

A new and distinct cultivar of Gerbera plant named Tertala, characterized by its semi-double type and flat flower form, pink ray floret color and pink perianth lobe color and 60–69 mm overall flower diameter.

1 Drawing Sheet

The present invention comprises a new and distinct cultivar of Gerbera, botanically known as *Gerbera jamesonii*, and referred to by the cultivar name Tertala.

Tertala was originated from a hybridization made in a controlled breeding program in De Kwakel, The Netherlands in 1988 under the supervision of the inventor Lambertus J. M. Stravers.

The female parent was a cultivar identified as 87.442. The male parent was a cultivar identified as M88.330. The new cultivar was discovered and selected as one flowering plant within the progeny of the stated parentage by the inventor on or about January 1989 in a controlled environment in De Kwakel.

The first asexual reproduction of Tertala was accomplished when vegetative cuttings were taken from the initial selection in April 1989 in a controlled environment in De Kwakel, The Netherlands by applicant. Horticultural examination of selected units initiated in November 1989 has demonstrated that the combination of characteristics as herein disclosed for Tertala are firmly fixed and are retained through successive generations of asexual reproduction. The new cultivar is presently being propagated both by cuttings and tissue culture.

Tertala has not been observed under all possible environmental conditions. The phenotype may vary significantly with variations in environment such as temperature, light intensity and day length. The following observations, measurements and comparisons describe plants grown in the greenhouses of Terra Nigra BV in De Kwakel, The Netherlands under greenhouse conditions which closely approximate those generally used in commercial practice.

The following traits have been repeatedly observed and have been determined to be basic characteristics of Tertala, which in combination distinguish this gerbera as a new and distinct cultivar:

1. Semi-double type with flat flower form.
2. Pink ray floret color.
3. Dark purple disc florets.
4. Pink perianth lobe color.
5. Total diameter of flower head from 60–69 mm.

Of the many commercial cultivars known to the present inventor, there is no cultivar sufficiently similar to Tertala in significant respects to provide a meaningful basis for comparison.

The accompanying photographic drawing shows typical inflorescence and foliage characteristics of Tertala, with the colors being as nearly true as possible with illustrations of this type. The photograph comprises a closeup view of the flower form and color of the new cultivar.

In the following description, color references are made to The Royal Horticultural Society Colour Chart (R.H.S.). The color values were determined at approximately 12:00 noon on Nov. 9, 1990 under artificial light at De Kwakel, The Netherlands.

Classification:

*Botanical.*—*Gerbera jamesonii* cv Tertala.

*Commercial.*—Gerbera.

Parentage: Seedling from cross of cultivars designated 87.442 and M88.330.

Plant: The plant when fully grown reaches a height of 40 cm.

Leaf blade:

*Length.*—Short, 40–45 cm.

*Width.*—Narrow, 14 cm.

*Thickness.*—Medium.

*Blistering (puckering).* Medium.

*Pubescence on upper side.*—Medium (midrib excluded).

*Depth of cuts or incisions in leaf.*—*Near bottom or base: Strong. Near middle: Medium. Near tip: Weak.*

*Color.*—Upper surface of leaf, medium green 137A; lower surface, light green.

*Glossiness on upper side.*—Weak.

*Angle at tip.*—Acute.

*Shape at tip.*—Pointed.

*Margin of lobes.*—Serrate.

*Petiole length.*—Medium, 10 cm.

*Petiole anthocyanin coloration.*—Present, medium in intensity.

Peduncle:

*Length.*—Short, 55 cm.

*Cross section.*—Round medium strength and thickness.

*Tendency to fasciation.*—Absent.

*Pubescence.*—Medium.

*Color.*—Medium green.

*Anthocyanin.*—Present at base, medium in intensity, none present at tip.

*Involucral bracts.*—Absent.

Flower head:

*Type.*—Semi-double with dark purple center; flat shaped in form.

*Diameter from edge to edge.*—60–69 mm.

*Height.*—From point of attachment of involucre to top of flower head is medium, 22 mm.

*Involucre.*—Height: Medium, 16 mm. Diameter: Small, 23 mm. Number of bracts: 36; longitudinal axis on inner rows are straight. Anthocyanin: Present at top of inner bracts. Pubescence: Weak.

*Outer row ray florets.*—Number in outer row: 40–60. Length of floret: Under 29 mm. Width of floret: 5–9 mm. Shape of floret: Longitudinal folding is strong. Cross section of floret: Flat. Length of free petals: Under 30 mm. Color distribution on inner side: Uniform; edge is similar color. Striation: Absent. Claw spot: Present. Color on top side: 48C. Color on bottom side: 49B. Angle of apex: Obtuse. Shape of apex:

Rounded. Incisions of apex: Present, two in number; shallow in depth.

Disc florets.—Diameter: 10–19 mm. Main color of perianth lobes: Pink for both male and female flowers. Color (mature and immature): Dark purple.

Reproductive parts:

*Stigma.*—Main color, white.

*Anthers.*—Main color: Yellow; color at top lighter relative to other part. Longitudinal striping: Present.

*Pappus.*—Main color: Yellow; color at top darker relative to other part. Orientation: Level of top is the same relative to closed disc florets.

I claim:

1. A new and distinct cultivar of Gerbera plant named Tertala, as illustrated and described.

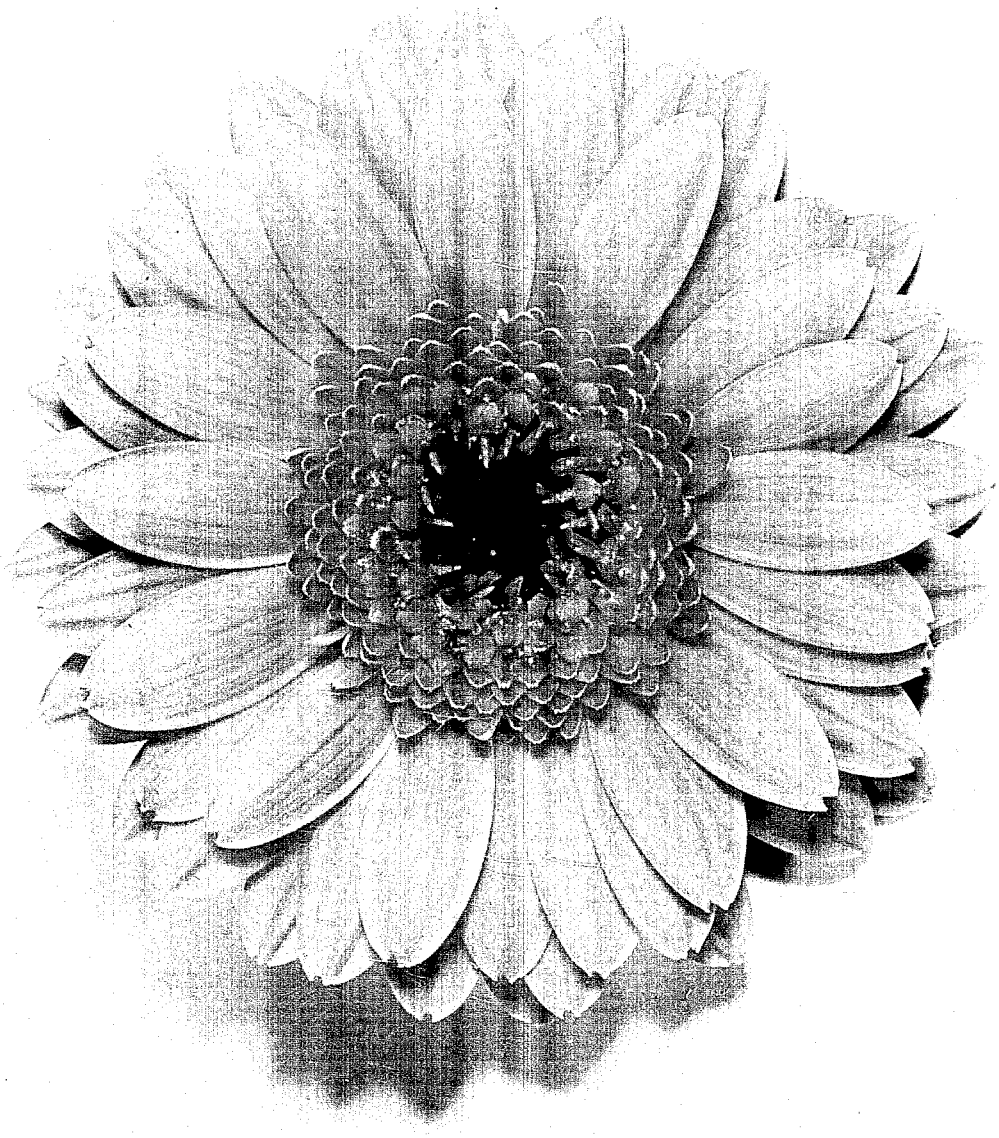

* * * * *